United States Patent
Schmitzer et al.

(10) Patent No.: US 10,154,667 B2
(45) Date of Patent: Dec. 18, 2018

(54) BROADLEAF CROP CONTROL WITH 6-ARYLPICOLINE CARBOXYLIC ACIDS, 2-ARYLPYRIMIDINE CARBOXYLIC ACIDS, OR SALTS OR ESTERS THEREOF

(71) Applicant: Dow AgroSciences LLC, Indianapolis, IN (US)

(72) Inventors: Paul Richard Schmitzer, indianapolis, IN (US); Kent William Davies, Campinas (BR); Monte Ray Weimer, Pittsboro, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 133 days.

(21) Appl. No.: 14/190,846

(22) Filed: Feb. 26, 2014

(65) Prior Publication Data

US 2014/0274715 A1 Sep. 18, 2014

Related U.S. Application Data

(60) Provisional application No. 61/781,328, filed on Mar. 14, 2013.

(51) Int. Cl.
*A01N 43/40* (2006.01)
*A01N 43/00* (2006.01)

(52) U.S. Cl.
CPC .................................. *A01N 43/40* (2013.01)

(58) Field of Classification Search
CPC .................................................... A01N 43/00
See application file for complete search history.

(56) References Cited

U.S. PATENT DOCUMENTS

| | | | |
|---|---|---|---|
| 6,239,072 B1 | 5/2001 | Flint et al. |
| 6,784,137 B2 | 8/2004 | Balko et al. |
| 7,314,849 B2 | 1/2008 | Balko et al. |
| 7,538,214 B2 | 5/2009 | Epp et al. |
| 7,776,044 B2 | 8/2010 | Epp et al. |
| 7,888,287 B2 | 2/2011 | Epp et al. |
| 2005/0044587 A1 | 2/2005 | Gabard et al. |
| 2006/0183637 A1 | 8/2006 | Loughner et al. |
| 2009/0221856 A1 | 9/2009 | Tobler et al. |
| 2010/0137137 A1 | 6/2010 | Rosinger et al. |
| 2011/0183845 A1 | 7/2011 | Loughner et al. |
| 2011/0287932 A1 | 11/2011 | Hacker et al. |
| 2011/0294663 A1 | 12/2011 | Hacker et al. |
| 2012/0053053 A1 | 3/2012 | Abdelouahab et al. |
| 2012/0071320 A1 | 3/2012 | Atkinson |
| 2012/0115727 A1 | 5/2012 | Satchivi et al. |
| 2012/0190551 A1 | 7/2012 | Yerkes et al. |
| 2012/0284812 A1 | 11/2012 | Mankin et al. |
| 2013/0023413 A1 | 1/2013 | Hacker et al. |

FOREIGN PATENT DOCUMENTS

| | | | |
|---|---|---|---|
| CN | 101360703 A | | 2/2009 |
| KZ | 6554 | | 10/2001 |
| UZ | 4048 A3 | | 11/2009 |
| WO | WO 2005/041669 A1 | * | 5/2005 |
| WO | WO 2007/017256 | * | 2/2007 |
| WO | WO 2007/053482 | * | 5/2007 |
| WO | WO 2007/082098 | * | 7/2007 |
| WO | 2007092184 | | 8/2007 |
| WO | WO 2007/092184 | * | 8/2007 |
| WO | 2009029518 A2 | | 3/2009 |
| WO | WO 2010/092339 | * | 8/2010 |
| WO | WO 2010/125332 A1 | * | 11/2010 |
| WO | WO 2011/066382 A1 | * | 6/2011 |
| WO | 2012018885 A1 | | 2/2012 |
| WO | 2012037425 | | 3/2012 |
| WO | 2014116894 A1 | | 7/2014 |

OTHER PUBLICATIONS

Synthesis of Esters: Esterification Reactions (retrieved online on Mar. 8, 2014 via google.com; p. 1).*
Steglich Esterification with DCC (retrieved online on Mar. 9, 2014 via google.com; p. 1-2).*
International Search Report and Written Opinion received in related International Application No. PCT/US2014/018740, dated Jun. 2, 2014.
Office Action issued in related CN Application No. 201480027391.4 dated Sep. 23, 2016.
Supplementary European Search Report issued in related EP Application No. 14776502.8 dated Oct. 10, 2016.
Office Action issued in Counterpart Application No. 2015/1094.1 dated Nov. 25, 2016.
Examination Report issued in Counterpart Application No. 2014/242095, dated Dec. 14, 2016.

* cited by examiner

*Primary Examiner* — Mina Haghighatian
*Assistant Examiner* — Mei Ping Chui
(74) *Attorney, Agent, or Firm* — Meunier Carlin & Curfman, LLC

(57) ABSTRACT

Disclosed herein are methods of controlling a broadleaf volunteer crop, comprising applying to the broadleaf volunteer crop, an area adjacent the broadleaf volunteer crop, or to soil or water to prevent the emergence or growth of the broadleaf volunteer crop, a herbicidally effective amount of a 6-arylpicoline carboxylic acid, a 2-arylpyrimidine carboxylic acid, or a salt or ester thereof, wherein the broadleaf volunteer crop is genetically modified soybean.

16 Claims, No Drawings

BROADLEAF CROP CONTROL WITH 6-ARYLPICOLINE CARBOXYLIC ACIDS, 2-ARYLPYRIMIDINE CARBOXYLIC ACIDS, OR SALTS OR ESTERS THEREOF

CROSS-REFERENCE TO RELATED APPLICATIONS

This application claims the benefit of priority to U.S. Provisional Patent Application No. 61/781,328, filed Mar. 14, 2013, which is herein incorporated by reference in its entirety.

FIELD OF THE DISCLOSURE

The present disclosure relates to methods of controlling growth of broadleaf crops using herbicidal compositions comprising a herbicidally effective amount of a 6-arylpicoline carboxylic acid, a 2-arylpyrimidine carboxylic acid, or an agriculturally acceptable salt or ester thereof.

BACKGROUND

Many recurring problems in agriculture involve controlling the growth of undesirable vegetation that can, for instance, negatively affect the growth of desirable vegetation. To help control undesirable vegetation, researchers have produced a variety of chemicals and chemical formulations effective in controlling such unwanted growth. However, a continuing need exists for new methods to control growth of undesirable vegetation, including volunteer crops. This has particularly become a problem as more volunteer crops are herbicide tolerant, thereby making them more difficult to eradicate. Some countries in South America now even mandate the eradication of volunteer soybeans, which may also be herbicide tolerant (HT), to limit the potential host organism from spreading soybean rust.

SUMMARY OF THE DISCLOSURE

A method of controlling a broadleaf volunteer crop is disclosed, comprising applying to the broadleaf volunteer crop, an area adjacent the broadleaf volunteer crop, or to soil or water to prevent the emergence or growth of the broadleaf volunteer crop, a herbicidally effective amount of a herbicide of Formula (I) or its salts or esters:

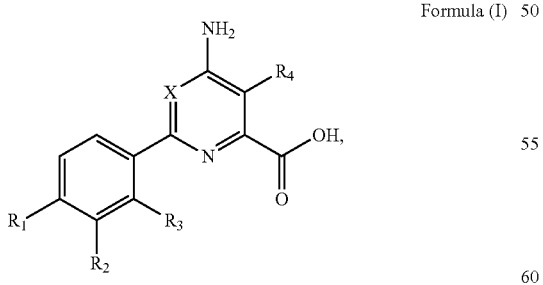

Formula (I)

wherein
$R^1$ is halogen, trifluoromethyl, cyano, substituted or unsubstituted $C_1$-$C_4$ alkyl, or substituted or unsubstituted $C_{1\text{-}C4}$ alkoxy;
$R^2$ is hydrogen, halogen, trifluoromethyl, cyano, substituted or unsubstituted $C_1$-$C_4$ alkyl, substituted or unsubstituted $C_2$-$C_4$ alkenyl, substituted or unsubstituted $C_2$-$C_4$ alkynyl, or substituted or unsubstituted $C_1$-$C_4$ alkoxy;
$R^3$ is hydrogen, halogen, substituted or unsubstituted $C_1$-$C_4$ alkyl, or substituted or unsubstituted $C_1$-$C_4$ alkoxy;
$R^4$ is halogen, substituted or unsubstituted $C_1$-$C_4$ alkyl, substituted or unsubstituted $C_{2\text{-}4}$ alkenyl, substituted or unsubstituted $C_2$-$C_4$ alkynyl, or substituted or unsubstituted $C_1$-$C_4$ alkoxy; and
X is N or $CR^5$, wherein $R^5$ is hydrogen or halogen, and wherein optionally $R^1$ and $R^2$ are combined to form —OCH$_2$O, —OCHFO—, or —OCF$_2$O—,
wherein the broadleaf volunteer crop is genetically modified.

In some embodiments, X is $CR^5$. The herbicide can have a structure of Formula (II) or its salts or esters:

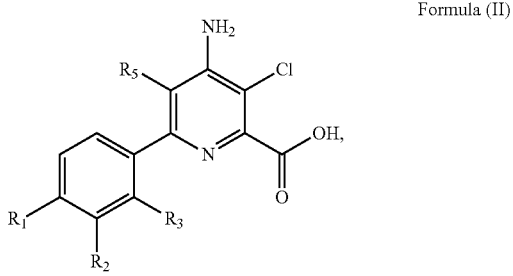

Formula (II)

wherein
$R^1$ is halogen or methyl;
$R^2$ is hydrogen, methyl, or methoxy;
$R^3$ is hydrogen, halogen, or methoxy; and
$R^5$ is hydrogen or fluoro,
wherein optionally $R^1$ and $R^2$ can combine to form —OCH$_2$O—.

In some embodiments, the herbicide is selected from the group consisting of Formulas (III) and (IV) or their respective salts or esters:

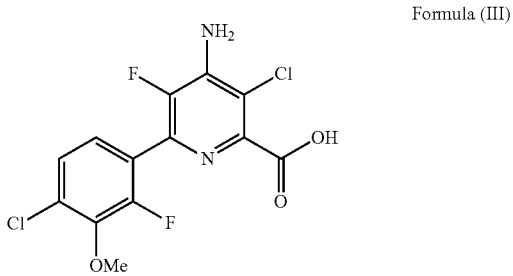

Formula (III)

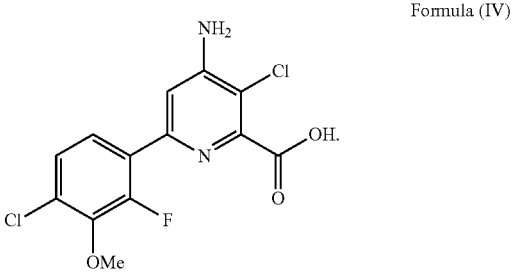

Formula (IV)

For example, the herbicide can be a benzyl ester of Formula (III) or a methyl ester of Formula (IV).

In some embodiments, the herbicide is selected from the group consisting of Formulas (V)-(IX) or their respective salts or esters:

Formula (V)

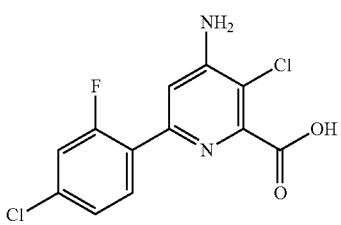

Formula (VI)

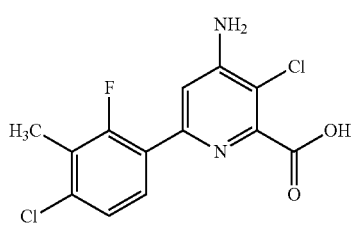

Formula (VII)

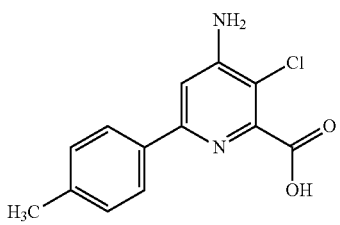

Formula (VIII)

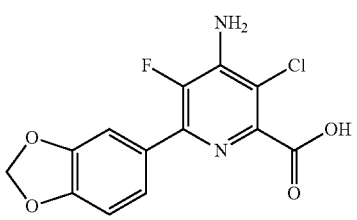

Formula (IX)

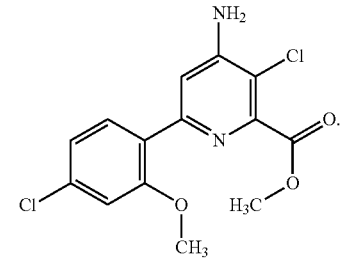

The broadleaf volunteer crop can be selected from the group consisting of soybean, canola, sunflower, sugar beets, alfalfa, and cotton. In some embodiments, the broadleaf volunteer crop is soybean, and the soybean can be infected with soybean rust. In some embodiments, the broadleaf volunteer crop is a glyphosate tolerant crop, contains an AAD-12 gene, is acetolactate synthase (ALS) resistant, or is 2,4-D resistant. In some embodiments, the broadleaf volunteer crop is present in a grassy crop, and the grassy crop is tolerant to the herbicide. The herbicide can be applied to the broadleaf volunteer crop prior to the emergence of the grassy crop. In some embodiments, the broadleaf volunteer crop is present in a corn crop, a wheat crop, or fallow. The treated broadleaf volunteer crop can have at least 96% brownout 14 days after application. In some embodiments, the treated broadleaf volunteer crop has substantially zero re-growth.

Although 6-arylpicoline and 2-arylpyrimidine carboxylic acids are known herbicides for controlling weeds, it was unexpected that these herbicides could control broadleaf crops with herbicide tolerance such as soybeans with very little regrowth, particularly at low application rates (e.g., less than 10 g ae/ha).

The description below sets forth details of one or more embodiment of the present disclosure. Other features, objects, and advantages will be apparent from the description and from the claims.

DETAILED DESCRIPTION

The present disclosure relates to methods for controlling undesirable broadleaf volunteer crops using herbicidal compositions comprising a 6-arylpicoline or a 2-arylpyrimidine carboxylic acid represented by general Formula (I), or an agriculturally acceptable salt or ester thereof:

Formula (I)

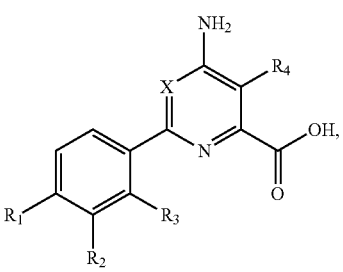

wherein
$R^1$ is halogen, trifluoromethyl, cyano, substituted or unsubstituted $C_1$-$C_4$ alkyl, or substituted or unsubstituted $C_1$-$C_4$ alkoxy;
$R^2$ is hydrogen, halogen, trifluoromethyl, cyano, substituted or unsubstituted $C_1$-$C_4$ alkyl, substituted or unsubstituted $C_2$-$C_4$ alkenyl, substituted or unsubstituted $C_2$-$C_4$ alkynyl, or substituted or unsubstituted $C_1$-$C_4$ alkoxy;
$R^3$ is hydrogen, halogen, substituted or unsubstituted $C_1$-$C_4$ alkyl, or substituted or unsubstituted $C_1$-$C_4$ alkoxy;
$R^4$ is halogen, substituted or unsubstituted $C_1$-$C_4$ alkyl, substituted or unsubstituted $C_2$-$C_4$ alkenyl, substituted or unsubstituted $C_2$-$C_4$ alkynyl, or substituted or unsubstituted $C_1$-$C_4$ alkoxy; and
X is N or $CR^5$, wherein $R^5$ is hydrogen or halogen, and wherein optionally $R^1$ and $R^2$ are combined to form —OCH$_2$O—, —OCHFO—, or —OCF$_2$O—.

The term "herbicide," as used herein, means an active ingredient that kills, controls, or otherwise adversely modifies the growth of vegetation. A "herbicidally effective amount" is an amount of an active ingredient that causes a "herbicidal effect," i.e., an adversely modifying effect and includes deviations from, for instance, natural development, killing, regulation, desiccation, and retardation. The terms "crops" and "vegetation" can include, for instance, germinant seeds, emerging seedlings, and established vegetation.

When X is $CR^5$ in Formula (I), the formula becomes Formula (Ia) that represents 6-arylpicoline carboxylic acids.

Formula (Ia)

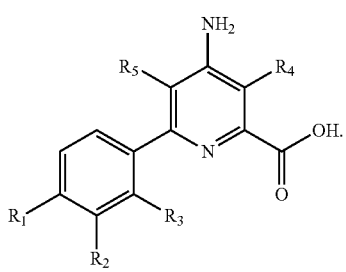

When X is N in Formula (I), the formula becomes Formula (Ib) that represents arylpyrimidine carboxylic acids.

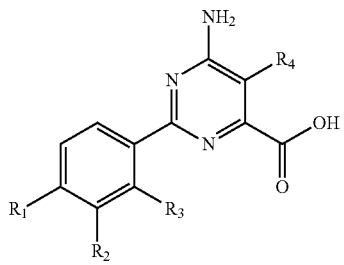
Formula (Ib)

In some embodiments, a 6-arylpicoline carboxylic acid represented by formula (II), or its salts or esters, is used:

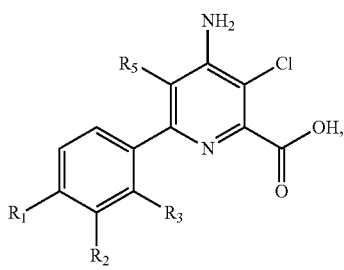
Formula (II)

wherein
$R^1$ is halogen or methyl;
$R^2$ is hydrogen, methyl, or methoxy;
$R^3$ is hydrogen, halogen, or methoxy; and
$R^5$ is hydrogen or fluoro,
wherein optionally $R^1$ and $R^2$ can combine to form —OCH$_2$O—.

In some embodiments, a 6-arylpicoline carboxylic acid represented by Formula (III) or (IV) is used:

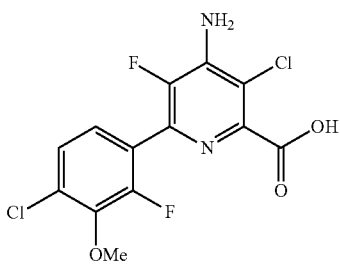 [SMILES: COc1c(Cl)ccc(-c2nc(C(=O)O)c(Cl)c(N)c2F)c1F]
Formula (III)

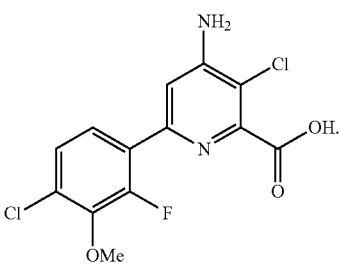
Formula (IV)

In some embodiments, a 6-arylpicoline carboxylic acid represented by Formulas (V)-(IX) is used:

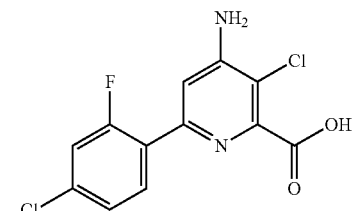
Formula (V)

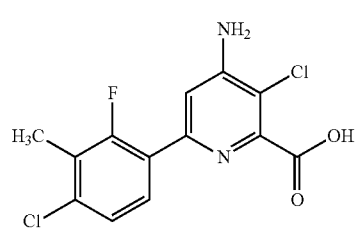
Formula (VI)

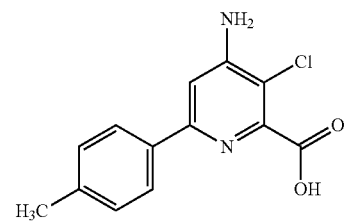
Formula (VII)

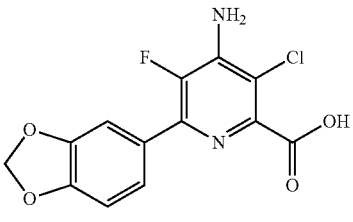
Formula (VIII)

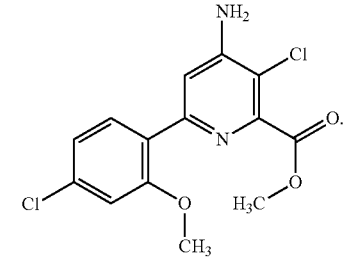
Formula (IX)

The compounds represented in Formula I and agriculturally acceptable salts and esters thereof, are synthetic herbicides used for a broad spectrum of weed control. The methods of making and using these compounds as herbicides are known in the art. See, e.g., U.S. Pat. No. 7,314,849 to Balko et al. and U.S. Pat. No. 7,538,214 to Epp et al.

The compound of Formula I can be provided in its acid form, or as an agriculturally acceptable salt or ester thereof. Exemplary agriculturally acceptable salts of the compounds of Formula I include, but are not limited to, sodium salts, potassium salts, ammonium salts or substituted ammonium salts, in particular mono-, di-, and tri-$C_1$-$C_8$-alkylammonium salts such as methyl ammonium, dimethylammonium, triethylammonium, and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, triisopropanolammonium salts, olamine salts, and diglycolamine salts.

In some embodiments, the compound of Formula I can be provided as an agriculturally acceptable ester. Suitable esters include, but are not limited to, $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, butotyl, 2-ethylhexyl and butoxyethyl esters, and aryl esters such as benzyl. Exemplary agriculturally acceptable esters include the methyl ester of 4-amino-3-chloro-6-(4-chloro-2-fluoro-3-methoxyphenyl)pyridine-2-carboxylic acid and the benzyl ester of 4-amino-3-chloro-5-fluoro-6-(4-chloro-2-fluoro-3-methoxyphenyl)pyridine-2-carboxylic acid.

The compound represented by Formula I or an agriculturally acceptable salt or ester thereof can be applied to a broadleaf volunteer crop, an area adjacent the broadleaf volunteer crop, or to soil or water to prevent the emergence or growth of the broadleaf volunteer crop in an amount sufficient to induce a herbicidal effect. In some embodiments, the arylpicoline carboxylic acid represented by the formula above or an agriculturally acceptable salt or ester thereof is applied in an amount of 0.5 grams acid equivalent per hectare (g ae/ha) or greater (e.g., 1.0 g ae/ha or greater, 1.5 g ae/ha or greater, 2.0 g ae/ha or greater, 2.5 g ae/ha or greater, 3.0 g ae/ha or greater, 4.0 g ae/ha or greater, 5.0 g ae/ha or greater, 6.0 g ae/ha or greater, 7.0 g ae/ha or greater, 8.0 g ae/ha or greater, 9.0 g ae/ha or greater, 10 g ae/ha or greater, 11 g ae/ha or greater, 12 g ae/ha or greater, 13 g ae/ha or greater, 14 g ae/ha or greater, or 15 g ae/ha or greater). In some embodiments, the compound represented by Formula I or an agriculturally acceptable salt or ester thereof can be applied in an amount of 20 g ae/ha or less (e.g., 18 g ae/ha or less, 15 g ae/ha or less, 14 g ae/ha or less, 13 g ae/ha or less, 12 g ae/ha or less, 11 g ae/ha or less, 10 g ae/ha or less, 9.0 g ae/ha or less, 8.0 g ae/ha or less, 7.0 g ae/ha or less, 6.0 g ae/ha or less, 5.0 g ae/ha or less, 4.0 g ae/ha or less, 3.0 g ae/ha or less, 2.5 g ae/ha or less, 2.0 g ae/ha or less, or 1.0 g ae/ha or less).

The compound represented by Formula I above or an agriculturally acceptable salt or ester thereof can be applied in an amount ranging from any of the minimum values described above to any of the maximum values described above. In some embodiments, the compound represented by Formula I or an agriculturally acceptable salt or ester thereof is applied in an amount of from 0.5-20 g ae/ha (e.g., from 1.0-18 g ae/ha, from 1.5-15 g ae/ha, from 2.0-12 g ae/ha, or from 3.0-10 g ai/ha). In some embodiments, the compound represented by Formula I is applied in an amount of less than 10 g ae/ha.

Formulations

The present disclosure also relates to formulations of the compositions and methods disclosed herein. In some embodiments, the formulation comprising the compound of Formula I, or an agriculturally acceptable salt or ester thereof, is present in suspended, emulsified, or dissolved form. Exemplary formulations include, but are not limited to, aqueous solutions, suspensions, also highly-concentrated aqueous, oily or other suspensions or dispersions, aqueous emulsions, aqueous microemulsions, aqueous suspo-emulsions, oil dispersions, and pastes.

The compositions and methods disclosed herein can also be mixed with or applied with an additive. In some embodiments, the additive can be diluted in water or can be concentrated. In some embodiments, the additive is added sequentially. In some embodiments, the additive is added simultaneously. In some embodiments, the additive is premixed with the compound of Formula I, or an agriculturally acceptable salt or ester thereof. In some embodiments, the additive is an additional pesticide. Exemplary additional pesticides include, but are not limited to, 2,4-dichlorophenoxyacetic acid (2,4-D), acetochlor, aclonifen, amicarbazone, amidosulfuron, aminocyclopyrachlor, aminotriazole, ammonium thiocyanate, asulam, atrazine, beflubutamid, benazolin, bensulfuron-methyl, bentazone, bifenox, bromacil, bromoxynil, butachlor, butafenacil, butralin, butroxydim, carbetamide, carfentrazone, carfentrazone-ethyl, chlormequat, clopyralid, chlorsulfuron, chlortoluron, cinidon-ethyl, clethodim, clodinafop-propargyl, clomazone, cyanazine, cyclosulfamuron, cycloxydim, cyhalofop-butyl, dicamba, dichlobenil, dichlorprop-P, diclofop-methyl, diclosulam, diflufenican, diflufenzopyr, dimefuron, dimethachlor, diquat, diuron, S-ethyl dipropylcarbamothioate (EPTC), ethoxysulfuron, fenoxaprop, fenoxaprop-ethyl, fenoxaprop-ethyl+isoxadifen-ethyl, fenoxaprop-P-ethyl, fenoxasulfone, flazasulfuron, florasulam, fluazifop, fluazifop-P-butyl, flucarbazone, flucarbazone-sodium, flucetosulfuron (LGC-42153), flufenacet, flumetsulam, flumioxazin, flupyrsulfuron, fluorochloridone, fluoroxypyr, fluoroxypyr-meptyl, flurtamone, glufosinate, glufosinate-ammonium, glyphosate, haloxyfop-methyl, haloxyfop-R, hexazinone, imazamethabenz, imazamox, imazapic, imazapyr, imazaquin, imazethapyr, imazosulfuron, indanofan, indaziflam, iodosulfuron, iodosulfuron-ethyl-sodium, ioxynil, isoproturon, isoxaben, isoxaflutole, lactofen, linuron, 2-methyl-4-chlorophenoxyacetic acid (MCPA), MCPB, mecoprop-P, mesosulfuron, mesosulfuron-ethyl sodium, metazochlor, metosulam, metribuzin, metsulfuron, metsulfuron-methyl, MSMA, napropamide, norfurazon, orthosulfamuron, oryzalin, oxadiargyl, oxadiazon, oxyfluorfen, paraquat, pendimethalin, penoxsulam, picloram, picolinafen, pinoxaden, primisulfuron, profluazol, propaquizafop, propoxycarbazone, propyzamide, prosulfocarb, prosulfuron, pyraflufen ethyl, pyrasulfotole, pyribenzoxim (LGC-40863), pyroxsulam, pyroxasulfone, quinmerac, quizalofop-ethyl-D, quizalofop-P-ethyl, quizalofop-P-tefuryl, rimsulfuron, sethoxydim, simazine, sulfentrazone, sulfometuron, sulfosate, sulfosulfuron, tebuthiuron, tepraloxidim, terbacil, terbuthylazine, terbutryn, thiazopyr, thifensulfuron, thifensulfuron-methyl, topramezone, tralkoxydim, triasulfuron, tribenuron, tribenuron-methyl, triafamone, triclopyr, and trifluralin, and agriculturally acceptable salts, esters and mixtures thereof. In some embodiments, the additional pesticide includes 2,4-D, dicamba, glufosinate, glyphosate, MCPA, an acetolactate synthase (ALS) inhibitor (e.g., penoxsulam), or combinations thereof.

In some embodiments, the additive includes an agriculturally acceptable adjuvant. Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, safeners, adhesives (for instance, for use in seed formulations), surfactants, protective colloids, emulsifiers, tackifiers, and mixtures thereof. Exemplary agriculturally acceptable adjuvants include, but are not limited to, crop oil concentrate (mineral oil (85%)+emulsifiers (15%)), nonylphenol ethoxylate, benzylcocoalkyldimethyl quaternary ammonium salt, blend of petroleum hydrocarbon, alkyl esters, organic acid, and anionic surfactant, $C_9$-$C_{11}$ alkylpolyglycoside, phosphate alcohol ethoxylate, natural primary alcohol ($C_{12}$-$C_{16}$) ethoxylate, di-sec-butylphenol EO-PO block copolymer, polysiloxane-methyl cap, nonylphenol ethoxylate+urea ammonium nitrate, emulsified methylated seed oil, tridecyl alcohol (synthetic) ethoxylate (8 EO), tallow amine ethoxylate (15 EO), and PEG(400) dioleate-99.

In some embodiments, the additive is a safener that is an organic compound leading to better crop plant compatibility when applied with a herbicide. In some embodiments, the safener itself is herbicidally active. In some embodiments, the safener acts as an antidote or antagonist in the crop plants and can reduce or prevent damage to the crop plants. Exemplary safeners include, but are not limited to, AD-67 (MON 4660), benoxacor, benthiocarb, brassinolide, cloquintocet (mexyl), cyometrinil, cyprosulfamide, daimuron, dichlormid, dicyclonon, diethotate, dimepiperate, disulfoton, fenchlorazole, fenchlorazole-ethyl, fenclorim, flurazole, fluxofenim, furilazole, harpin proteins, isoxadifen-ethyl, jiecaowan, jiecaoxi, mefenpyr, mefenpyr-diethyl, mephenate, naphthalic anhydride, 2,2,5-trimethyl-3-(dichloroacetyl)-1,3-oxazolidine, 4-(dichloroacetyl)-1-oxa-4-azaspiro[4.5]decane, oxabetrinil, R29148, and N-phenyl-sulfonylbenzoic acid amides, as well as agriculturally acceptable salts and, provided they have a carboxyl group, their agriculturally acceptable derivatives thereof. In some embodiments, the safener can be cloquintocet or an ester or salt thereof, such as cloquintocet (mexyl).

Exemplary additional surfactants (e.g., wetting agents, tackifiers, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophobically modified starches, polyvinyl alcohol, polycarboxylates, polyalkoxylates, polyvinyl amine, polyethyleneimine, polyvinylpyrrolidone and copolymers thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivates, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamine B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

In some embodiments, the additive includes a carrier. In some embodiments, the additive includes a liquid carrier. In some embodiments, the additive includes an organic or inorganic carrier. Exemplary liquid carriers include, but are not limited to, petroleum fractions or hydrocarbons such as mineral oil, aromatic solvents, paraffinic oils, and the like or less, vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like or less, esters of the above vegetable oils or less, esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like or less, esters of mono, di and polycarboxylic acids and the like, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like, and water as well as mixtures thereof.

In some embodiments, emulsions, pastes or oil dispersions, can be prepared by homogenizing the compound of Formula I, or an agriculturally acceptable salt or ester thereof, in water, optionally by means of wetting agent, tackifier, dispersant or emulsifier. In some embodiments, concentrates suitable for dilution with water are prepared, comprising the compound of Formula I, or an agriculturally acceptable salt or ester thereof, and optionally a wetting agent, a tackifier, and/or a dispersant or emulsifier.

The concentration of the compound of Formula I, or an agriculturally acceptable salt or ester thereof, in the formulations can be varied. In some embodiments, the formulations comprise from 1% to 95% (e.g., from 5% to 95%, from 10% to 80%, from 20% to 70%, from 30% to 50%) by total weight of the compound of Formula I, or an agriculturally acceptable salt or ester thereof. In some embodiments, the compound of Formula I, or an agriculturally acceptable salt or ester thereof, can be employed at a purity of from 90% to 100% (e.g., from 95% to 100%) according to nuclear magnetic resonance (NMR) spectrometry.

Methods of Application

The compositions disclosed herein can be applied in any known technique for applying herbicides. Exemplary application techniques include, but are not limited to, spraying, atomizing, or direct application into water (in-water). The method of application can vary depending on the intended purpose. In some embodiments, the method of application can be chosen to ensure the finest possible distribution of the compositions disclosed herein.

The compositions disclosed herein can be applied after seeding and before or after the emergence of the crop plants. In some embodiments, the compositions disclosed herein are applied to the broadleaf crop or an area adjacent to the broadleaf crop, or applied to soil or water to prevent the emergence or growth of the broadleaf crop by spraying (e.g., foliar spraying). In some embodiments, the spraying techniques use, for example, water as carrier and spray liquor rates of from 0.5 liters per hectare (L/ha) to 2000 L/ha (e.g., from 0.5 L/ha to 50 L/ha, from 50 L/ha to 1000 L/ha, or from 100 to 500 L/ha).

In some embodiments, the herbicidal activity to the broadleaf crop is exhibited by the compound of Formula I, or an agriculturally acceptable salt or ester thereof, when it is applied directly to the broadleaf crop or to the locus of the broadleaf crop at any stage of growth or before planting or emergence. The effect observed can depend upon the type of undesirable crop to be controlled, the stage of growth of the undesirable crop, the application parameters of dilution and spray drop size, the environmental conditions at the time of use, the specific compound employed, the specific adjuvants and carriers employed, the soil type, and the like, as well as the amount of chemical applied. In some embodiments, these and other factors can be adjusted to promote non-selective or selective herbicidal action.

The compositions and methods disclosed herein are effective against a variety of types of undesirable vegetation. In some embodiments, the compositions disclosed herein can be used for controlling broadleaf volunteer crops such as soybean, canola, sunflower, sugar beets, alfalfa, and cotton. For example, the compositions disclosed herein can be used to control broadleaf volunteer crops, such as those infected with soybean rust. The compositions and methods disclosed herein can particularly be used to control broadleaf crop plants that are resistant to, for instance, herbicides, pathogens, and/or insects. Accordingly, the compositions and methods disclosed herein can be used in broadleaf crop plants that are resistant to one or more herbicides because of genetic engineering or breeding. In some embodiments, the compositions and methods disclosed herein can be used to control broadleaf volunteer crop plants that are resistant to one or more pathogens such as plant pathogenous fungi owing to genetic engineering or breeding. In some embodiments, the compositions and methods disclosed herein can be used to control broadleaf volunteer crop plants that are resistant to attack by insects owing to genetic engineering or breeding. The broadleaf volunteer crops can be resistant to synthetic auxins or, owing to introduction of the gene for *Bacillus thuringiensis* (or Bt) toxin by genetic modification, are resistant to attack by certain insects. In some embodiments, the broadleaf volunteer crops are tolerant to glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, bromoxynil, or combinations thereof. In some embodiments, the broadleaf volunteer crops can possess multiple or stacked traits conferring tolerance to multiple chemistries and/or multiple modes of action. In some embodiments, the broadleaf volunteer crop is a glyphosate tolerant crop such as glyphosate tolerant soybean crop. In some embodiments, the broadleaf volunteer crop contains an AAD-12 gene. In some embodiments, the broadleaf volunteer crop is acetolactate synthase (ALS) inhibitor resistant. In some embodiments, the broadleaf volunteer crop is 2,4-D resistant.

The broadleaf volunteer crop to be controlled can be present in a grassy crop. In some embodiments, the grassy crop is a corn crop, a wheat crop, rice or fallow. In some embodiments, the broadleaf volunteer soybean crop is infected with soybean rust. In some embodiments, the grassy crop can be resistant to, for instance, herbicides, pathogens, and/or insects. Accordingly, the compositions and methods disclosed herein can be used in grassy crops that are resistant to one or more herbicides because of genetic engineering or breeding. In some embodiments, the compositions and methods disclosed herein can be used in grassy crop plants that are resistant to one or more pathogens such as plant pathogenous fungi owing to genetic engineering or breeding. In some embodiments, the compositions and methods disclosed herein can be used in grassy crop plants that are resistant to attack by insects owing to genetic engineering or breeding. In some embodiments, the grassy crop plants are resistant to synthetic auxins or, owing to introduction of the gene for *Bacillus thuringiensis* (or Bt) toxin by genetic modification, are resistant to attack by certain insects. In some embodiments, the compositions and methods described herein also can be used in conjunction with glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil to control vegetation in grassy crops tolerant to glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, bromoxynil, or combinations thereof. In some embodiments, the broadleaf volunteer crops are controlled in grassy crops possessing multiple or stacked traits conferring tolerance to multiple chemistries and/or multiple modes of action. In some embodiments, the grassy crop contains an AAD-12 gene. In some embodiments, the grassy crop is acetolactate synthase (ALS) inhibitor resistant. In some embodiments, the grassy crop is 2,4-D resistant. In some embodiments, the grassy crop is HPPD inhibitor resistant. In some embodiments, the grassy crop is glufosinate resistant. In some embodiments, the grassy crop is tolerant to the compounds represented by Formula (I). In some embodiments, the compounds of Formula (I) are applied to the broadleaf volunteer crop prior to the emergence of the grassy crop.

Exemplary treatment areas can be areas where grasses and broadleaf volunteer crops may be present and include, but are not limited to, turfgrass, pastures, grasslands, rangelands, fallow land, rights of way, aquatic settings, wildlife management areas, and non-irrigation ditchbanks. In some embodiments, the compositions and methods disclosed herein can be used in industrial vegetation management (IVM), for example, to control undesired vegetation along roadsides, power-lines, pipelines, rights-of-way, railways, well sites, and equipment yards. In some embodiments, the compositions and methods disclosed herein can be used to control undesirable vegetation in conservation reserve program lands (CRP), grasslands, and grasses grown for seed. In some embodiments, the compositions and methods disclosed herein can be used on lawns (e.g., residential, industrial, and institutional), golf courses, parks, cemeteries, athletic fields, and sod farms.

The compositions and methods disclosed herein can be used to control undesired vegetation. In some embodiments, the compositions and methods disclosed herein can be used to control undesired vegetation (e.g., to provide at least 70% control, to provide at least 75% control, to provide at least 80% control, to provide at least 85% control, to provide at least 90% control, to provide at least 95% control, or to provide at least 98% control) less than 35 days after application (e.g., less than 28 days, less than 25 days, less than 21 days, less than 18 days, less than 16 days, less than 14 days, less than 12 days, less than 10 days, less than 8 days, less than 7 days, less than 6 days, less than 5 days, or shorter). The control can be in the form of brownout of the crop, suppression of seed production, and combinations thereof. In some embodiments, the treated volunteer broadleaf crop has at least 96% brownout 14 days after application. In some embodiments, the broadleaf volunteer crop after it has been treated or controlled using the compound of Formula I, or a salt or ester thereof, has substantially no or no re-growth. In some embodiments, treating the broadleaf volunteer crop prevents or reduces seed production.

By way of non-limiting illustration, examples of certain embodiments of the present disclosure are given below.

EXAMPLES

Greenhouse Evaluation of Applications for Broadleaf Volunteer Crop Control

Test plants were grown in METRO-MIX® 360 (SunGro Horticulture, Bellevue, Wash.) in 132.7 square centimeters (cm²) plastic pots for 7-21 days in a greenhouse with an approximate 15 hour (h) photoperiod which was maintained at about 23-29° C. during the day and 22-28° C. during the night. Plants were grown to the 2 to 3 leaf stage prior to applications. Both conventional soybean crops varieties, Maverick and Resnick, and herbicide resistant (HT) varieties AAD12, AAD1, and ROUNDUP® ready soybean crops were treated.

A weighed amount, determined by the highest rate to be tested, of each test compound was placed in a 25 milliliter (mL) glass vial and was dissolved in 4 mL of a 97:3 v/v (volume/volume) mixture of acetone and dimethyl sulfoxide (DMSO), which will be referred to as General Purpose Solvent (GPS), to obtain concentrated stock solutions. If the test compound did not dissolve readily, the mixture was warmed and/or sonicated. The concentrated stock solutions obtained were diluted with 20 mL of an aqueous mixture containing water, GPS, isopropyl alcohol, ATPLUS® 411F crop oil concentrate, and TRITON® X-155 surfactant in a 46:42:12:1.0:0.02 v/v ratio to obtain spray solutions containing the highest application rates. Additional application rates were obtained by serial dilution of 12 mL of the high rate solution into a solution containing 2 mL of 97:3 v/v (volume/volume) mixture of acetone and dimethyl sulfoxide (DMSO) and 10 mL of an aqueous mixture containing water, GPS, isopropyl alcohol, ATPLUS® 411F crop oil concentrate, and TRITON® X-155 surfactant in a 46:42:12:1.0:0.02 v/v ratio to obtain 1/2X, 1/4X, 1/8X and 1/16X rates of the high rate (X). Compound requirements are based upon a 12 mL application volume at a rate of 187 L/ha. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 cm) above the average plant canopy height. Control plants were sprayed in the same manner with the solvent blank. The treated plants and control plants were placed in a greenhouse as described above and watered by sub-irrigation to prevent wash-off of the test compounds. After 21 days, the condition of the test plants as compared with that of the control plants was determined visually and scored on a scale of 0 to 100 percent where 0 corresponds to no injury and 100 corresponds to complete kill, and results are listed in Table 1 along with active ingredients and their respective formulations. Each score in Table 1 represents an average obtained from results of three representative experiments.

TABLE 1

Active Compound and Average Percent Crop Control after Treatment

| Active Compound | Rate (g ae/ha) | Conventional GLXMA | | HT Varieties GLXMA | | |
|---|---|---|---|---|---|---|
| | | Maverick | Resnick | AAD12 | AAD1 | RoundUp |
| [structure with NH₂, F, Cl, OMe, COOH] | 17.5 | 100 | 100 | 100 | | |
| | 8.75 | 100 | 100 | 100 | 100 | 100 |
| | 4.4 | 100 | 100 | 100 | 100 | 100 |
| | 2.2 | 95 | 92 | 93 | 100 | 93 |
| | 1.1 | 87 | 83 | 85 | 87 | 83 |
| [structure with NH₂, Cl, F, OMe, COO⁻K⁺] | 17.5 | 100 | 100 | 100 | 100 | 100 |
| | 8.75 | 100 | 100 | 100 | 100 | 100 |
| | 4.4 | 100 | 100 | 100 | 100 | 100 |
| | 2.2 | 100 | 100 | 100 | 100 | 100 |
| | 1.1 | 97 | 99 | 100 | 100 | 100 |

GLXMA: Glycine max (soybean)

Additional formulations with different 6-arylpicolinates were tested in the greenhouse on Maverick and RoundUp-ready soybean crops using the procedure described above.

The active ingredients and crop control scores are listed in Table 2. Each score in Table 2 represents an average obtained from results of three representative experiments.

TABLE 2

Active Compound and Average Percent Crop Control after Treatment

| Active Compound | Rate (g ae/ha) | Maverick GLXMA | RoundUp Ready GLXMA |
|---|---|---|---|
| 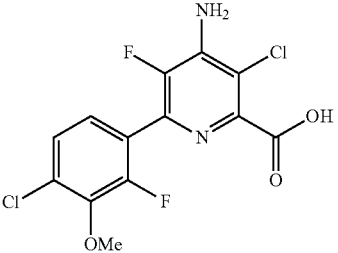 [SMILES: COc1c(Cl)ccc(-c2nc(C(=O)O)c(Cl)c(N)c2F)c1F] | 17.5<br>8.75<br>4.4<br>2.2<br>1.1 | 100<br>100<br>100<br>100<br>100 | 100<br>100<br>100<br>100<br>100 |
| 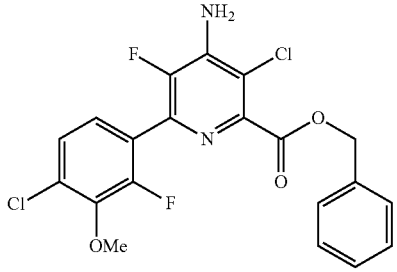 [SMILES: COc1c(Cl)ccc(-c2nc(C(=O)OCc3ccccc3)c(Cl)c(N)c2F)c1F] | 17.5<br>8.75<br>4.4<br>2.2<br>1.1 | 100<br>100<br>100<br>100<br>100 | 100<br>100<br>100<br>100<br>100 |
| 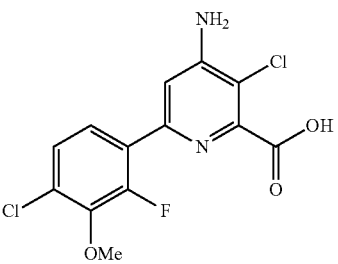 [SMILES: COc1c(Cl)ccc(-c2cc(N)c(Cl)c(C(=O)O)n2)c1F] | 17.5<br>8.75<br>4.4<br>2.2<br>1.1 | 100<br>100<br>100<br>100<br>100 | 100<br>100<br>100<br>100<br>100 |
| 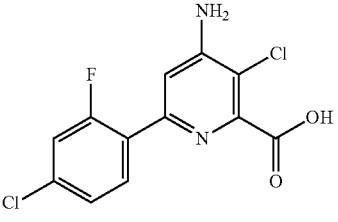 [SMILES: Nc1cc(-c2ccc(Cl)cc2F)nc(C(=O)O)c1Cl] | 17.5<br>8.75<br>4.4<br>2.2<br>1.1 | 100<br>100<br>100<br>100<br>100 | 100<br>100<br>100<br>100<br>100 |
| 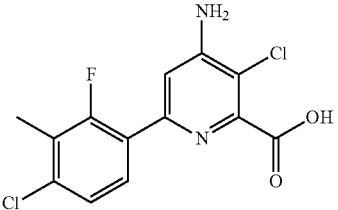 [SMILES: Cc1c(Cl)ccc(-c2cc(N)c(Cl)c(C(=O)O)n2)c1F] | 17.5<br>8.75<br>4.4<br>2.2<br>1.1 | 100<br>100<br>99<br>82<br>53 | 100<br>100<br>98<br>80<br>57 |

TABLE 2-continued

Active Compound and Average Percent Crop Control after Treatment

| Active Compound | Rate (g ae/ha) | Maverick GLXMA | RoundUp Ready GLXMA |
|---|---|---|---|
| 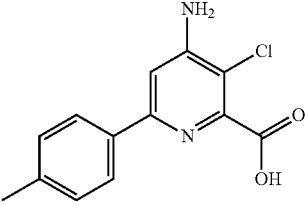 [SMILES: Cc1ccc(-c2cc(N)c(Cl)c(C(=O)O)n2)cc1] | 17.5<br>8.75<br>4.4<br>2.2<br>1.1 | 100<br>100<br>100<br>100<br>100 | 100<br>100<br>100<br>100<br>90 |
| 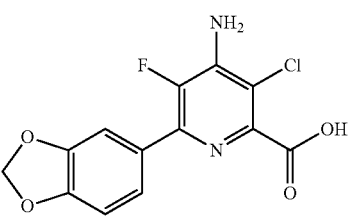 [SMILES: Nc1c(F)c(-c2ccc3c(c2)OCO3)nc(C(=O)O)c1Cl] | 17.5<br>8.75<br>4.4<br>2.2<br>1.1 | 100<br>95<br>58<br>42<br>27 | 98<br>92<br>73<br>45<br>32 |
| 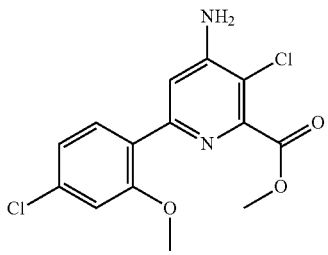 [SMILES: COC(=O)c1nc(-c2ccc(Cl)cc2OC)cc(N)c1Cl] | 17.5<br>8.75<br>4.4<br>2.2<br>1.1 | 100<br>100<br>100<br>100<br>98 | 100<br>100<br>100<br>99<br>95 |

GLXMA: Glycine max (soybean)

Representative compounds of Formula (I) have shown comparable herbicidal activity in both conventional as well as herbicidal resistant crop (HT) varieties, demonstrating the potential of these compounds in volunteer crop control.

Field Evaluation of Applications for Broadleaf Volunteer Crop Control

Field trials were conducted with post emergence applications made to broadleaf volunteer soybean crops. Both conventional soybean crops (GS14-15) and ROUNDUP® resistant soybean crops (GS15-16) were treated (20-40 per square meter).

The formulations included 4-amino-3-chloro-5-fluoro-6-(4-chloro-2-fluoro-3-methoxyphenyl)pyridine-2-carboxylic acid (formulation A), the benzyl ester of 4-amino-3-chloro-5-fluoro-6-(4-chloro-2-fluoro-3-methoxyphenyl)pyridine-2-carboxylic acid (formulation B), or the methyl ester of 4-amino-3-chloro-6-(4-chloro-2-fluoro-3-methoxyphenyl)pyridine-2-carboxylic acid (formulation C), with 2,4-D DMA used as a control (control formulation). The active ingredients and their respective formulations are listed in Table 3. The formulations were provided as suspension concentrates in water and applied with the adjuvant provided. Specifically, formulation A is applied at 100 g/L (9.48% w/w); formulation B is applied at AI=125.818 g/L (11.87% w/w); AE=100 g/L (9.43% w/w); formulation C is applied at AI=100 g/L (10% w/w) and AE=95.94 g/L (9.59% w/w); and the control formulation is applied at AI=806.03 g/L (65.74% w/w) and AE=669 g/L (54.57% w/w).

TABLE 3

Formulations Used in Crop Control

| Treatment No. | Formulations | Rate (g ae/ha) | Adjuvant |
|---|---|---|---|
| 1 | A | 1.125 | Treatments were applied |
| 2 | | 2.25 | with 1% v/v Joint Mineral |
| 3 | | 4.5 | oil (J'oil or BF-117). |
| 4 | | 9 | |
| 5 | | 18 | |
| 6 | B | 1.125 | |
| 7 | | 2.25 | |
| 8 | | 4.5 | |
| 9 | | 9 | |
| 10 | | 18 | |
| 11 | C | 1.125 | |
| 12 | | 2.25 | |
| 13 | | 4.5 | |
| 14 | | 9 | |
| 15 | | 18 | |
| 16 | Control | 1340 | — |
| 17 | Untreated | — | — |

The average percent control of several species of targeted plants (indicated by Bayer codes) at specified dates after treatment are provided in Tables 4 and 5 below. The data was the result of conducting factorial replicated field trials (4 trials) by applying the compositions at a spray pressure of 300 kilopascals (kPa) and a spray volume of 200 L/ha. The treated plots and control plots were visually rated blind at the specified dates after application. Ratings were based on a scale of 0-100%, as discussed above, wherein 0% indicates complete growth of the undesired vegetation and 100% indicates complete prevention/eradication of the undesired vegetation. The results are included in Table 4 below for average percent crop control after treatment and in Table 5 for average percent weed control after treatment.

At rates of 2.25 g ae/ha or greater, formulations 1-3 demonstrated acceptable control (>96% brownout at 14 daa) of large (4-6 leaf) volunteer conventional and glyphosate tolerant soybeans, equivalent to the commercial standard treatment with 2,4-D DMA at 1340 g ae/ha. The control was fast (>85% brownout at 7daa) and there was zero re-growth. The compositions were also effective in controlling wandering jew and wild poinsettia. These formulations therefore demonstrated potential for volunteer soybean control in fallow.

TABLE 4

Average Percent Crop Control after Treatment

| | Pest Bayer Code | | | | | | | |
|---|---|---|---|---|---|---|---|---|
| | GLXMA | GLXMA | GLXMA | GLXMA | GLXMA | GLXMA | GLXMA | GLXMA |
| | | | | Variety/Hybrid | | | | |
| | CONV. | GLY. TO | CONV. | GLY. TO | CONV | GLY. TO | CONV | GLY. TO |
| | | | | Trt-Eval Interval | | | | |
| Treatment No. | 8DAAA 1 | 8DAAA 2 | 14DAAA 3 | 14DAAA 4 | 21DAAA 5 | 21DAAA 6 | 28DAAA 7 | 28DAAA 8 |
| 1 | 76.3 | 65 | 94.3 | 80 | 86 | 66.3 | 91.3 | 72.5 |
| 2 | 92.3 | 87 | 100 | 98.3 | 98.8 | 93.5 | 100 | 97.8 |
| 3 | 97.3 | 95.8 | 100 | 99.8 | 99 | 98.8 | 100 | 100 |
| 4 | 98 | 96.5 | 100 | 100 | 99 | 99 | 100 | 100 |
| 5 | 98.5 | 98.5 | 100 | 100 | 99 | 99 | 100 | 100 |
| 6 | 82.5 | 78.8 | 98.3 | 93.8 | 95 | 85.8 | 97.8 | 91.3 |
| 7 | 92.5 | 83.8 | 100 | 97.5 | 99 | 93.5 | 100 | 95.8 |
| 8 | 97.3 | 91.8 | 100 | 99.8 | 99 | 97.3 | 100 | 100 |
| 9 | 97.3 | 94.3 | 100 | 100 | 99 | 98 | 100 | 100 |
| 10 | 98 | 95 | 100 | 99.8 | 99 | 98.8 | 100 | 100 |
| 11 | 82.5 | 70 | 98.8 | 90 | 94.8 | 81.3 | 99.5 | 85.8 |
| 12 | 93 | 87.5 | 100 | 99 | 99 | 96.5 | 100 | 100 |
| 13 | 96.8 | 92.5 | 100 | 100 | 99 | 99 | 100 | 100 |
| 14 | 98.3 | 95.8 | 100 | 100 | 99 | 99 | 100 | 100 |
| 15 | 98.3 | 97.5 | 100 | 100 | 99 | 99 | 100 | 100 |
| 16 | 98.3 | 98 | 100 | 100 | 99 | 98.5 | 100 | 100 |
| 17 | 0 | 0 | 0 | 0 | 0 | 0 | 0 | 0 |

GLXMA: Glycine max (soybean)
CONV: conventional
GLY. TO: glyphosate tolerant

TABLE 5

Average Percent Weed Control after Treatment

| Pest Bayer Code Treatment-Evaluation Interval Treatment No. | EPHHL 9DAAA 1 | COMBE 9DAAA 2 | COMBE 28DAAA 3 | EPHHL 28DAAA 4 |
|---|---|---|---|---|
| 1 | 61.3 | 72.5 | 71.3 | 52.5 |
| 2 | 72.5 | 76.3 | 83.3 | 75 |
| 3 | 75 | 87 | 90.8 | 89.3 |
| 4 | 84.3 | 94 | 93.8 | 93.8 |
| 5 | 90 | 95 | 100 | 97.5 |
| 6 | 55 | 68.8 | 66.3 | 62.5 |
| 7 | 66.3 | 80 | 79.3 | 70 |
| 8 | 71.3 | 86.3 | 84.5 | 83 |
| 9 | 80 | 86.3 | 86.3 | 86.3 |
| 10 | 80 | 91.3 | 95.8 | 97 |
| 11 | 60 | 48.8 | 38.8 | 57.5 |
| 12 | 71.3 | 68.8 | 56.3 | 80 |
| 13 | 73.8 | 72.5 | 62.5 | 96.3 |
| 14 | 82.5 | 81.3 | 82.5 | 95.8 |
| 15 | 85 | 86.3 | 90 | 100 |
| 16 | 71.3 | 87.5 | 90.8 | 85 |
| 17 | 0 | 0 | 0 | 0 |

EPHHL: Euphorbia heterophylla (wild poinsettia)
COMBE: Commelina benghalensis (day flower or wandering jew)
DAAA: days after application A Field Evaluation of Broadleaf Volunteer Crop Control with Various Herbicides The average percent visual control of ROUNDUP READY® soybeans (GLXMA) 46 days after treatment with various herbicides with standard formulation in comparison with compound of Formula (IV) at specified rates are provided in Table 6 below. The data was the result of conducting factorial replicated field trials (4 trials) by applying the compositions at a spray pressure of 300 kPa and a spray volume of 200 L/ha. The treated plots and control plots were visually rated blind at the specified dates after application. Ratings were based on a scale of 0-100%, as discussed above, wherein 0% indicates complete growth of the undesired vegetation and 100% indicates complete prevention/eradication of the undesired vegetation.

TABLE 6

Average Percent (%) Crop (GLXMA: Glycine max (soybean)) Control 46 Days After Treatment with Various Herbicides

| Herbicide | Rate (g ai/Ha) | % Crop Control |
|---|---|---|
| 2,4-D-dma | 1300 | 97.3 |
| Fluroxypyr | 200 | 100 |

TABLE 6-continued

Average Percent (%) Crop (GLXMA: *Glycine max* (soybean)) Control 46 Days After Treatment with Various Herbicides

| Herbicide | Rate (g ai/Ha) | % Crop Control |
|---|---|---|
| Flumioxazin | 25 | 0 |
| Paraquat | 300 | 85 |
| Metsulfuron | 6 | 98.3 |
| Pyroxsulam | 18 | 98.3 |
| Formula (IV) | 17 | 93 |
| Fluroxypyr + triclopyr | 40 + 120 | 99.5 |
| Clopyralid | 54 | 93.8 |
| Iodosulfuron | 3.5 | 90 |

The average percent visual control of RoundUp Ready® soybeans (GLXMA) 30 days after treatment with various herbicides with standard formulation in comparison with compound of Formula (III) at specified rates are provided in Table 7 below. The data was the result of conducting factorial replicated field trials (3 trials) by applying the compositions at a spray pressure of 300 kPa and a spray volume of 200 L/ha. The treated plots and control plots were visually rated blind at the specified dates after application. Ratings were based on a scale of 0-100%, as discussed above, wherein 0% indicates complete growth of the undesired vegetation and 100% indicates complete prevention/eradication of the undesired vegetation.

TABLE 7

Average Percent (%) Crop (GLXMA: *Glycine max* (soybean)) Control 30 Days After Treatment with Various Herbicides

| Herbicide | Rate (g ai/Ha) | % Crop Control |
|---|---|---|
| florasulam | 5 + 1% J'Oil | 63.3 |
| Metsulfuron | 6 | 89.3 |
| Metsulfuron | 6 + 1% J'Oil | 96 |
| Oxyfluorfen | 72 | 16.7 |
| Paraquat | 300 | 61.7 |
| Atrazine | 1500 | 75 |
| Atrazine | 1500 + 1% J'Oil | 86.7 |
| Penoxsulam | 18 | 87.3 |
| Formula (III) | 18 | 100 |
| Florasulam + clopyralid | 5 + 30 + 1% J'Oil | 86.3 |
| Aminopyralid TIPA | 1.25 | 60 |
| Untreated | 0 | 0 |

Compounds represented by Formula (I) such as Formula (III) and Formula (IV) have demonstrated comparable or superior herbicidal activity in genetically engineered crops as compared to other commercially known herbicides.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method of controlling the emergence or growth of a broadleaf volunteer crop, comprising:

applying to the broadleaf volunteer crop, an area adjacent the broadleaf volunteer crop, or to soil or water, a herbicidally effective amount of a herbicide of Formula (I) or its salts or esters:

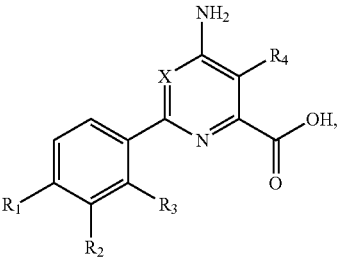

Formula (I)

wherein $R^1$ is halogen, trifluoromethyl, cyano, substituted or unsubstituted $C_1$-$C_4$ alkyl, or substituted or unsubstituted $C_1$-$C_4$ alkoxy;

$R^2$ is hydrogen, halogen, trifluoromethyl, cyano, substituted or unsubstituted $C_1$-$C_4$ alkyl, substituted or unsubstituted $C_2$-$C_4$ alkenyl, substituted or unsubstituted $C_2$-$C_4$ alkynyl, or substituted or unsubstituted $C_1$-$C_4$ alkoxy;

$R^3$ is hydrogen, halogen, substituted or unsubstituted $C_1$-$C_4$ alkyl, or substituted or unsubstituted $C_1$-$C_4$ alkoxy;

$R^4$ is halogen, substituted or unsubstituted $C_1$-$C_4$ alkyl, substituted or unsubstituted $C_2$-$C_4$ alkenyl, substituted or unsubstituted $C_2$-$C_4$ alkynyl, or substituted or unsubstituted $C_1$-$C_4$ alkoxy; and X is $CR^5$, wherein $R^5$ is hydrogen or halogen, and wherein optionally $R^1$ and $R^2$ are combined to form —OCH$_2$O, —OCHFO—, or —OCF$_2$O—, wherein the broadleaf volunteer crop is genetically modified; and wherein the broadleaf volunteer crop is soybean wherein the herbicidally effective amount of the herbicide of Formula (I) is at a rate of less than 10 g ae/ha.

2. The method of claim 1, wherein the herbicide has a structure of Formula (II) or its salts or esters:

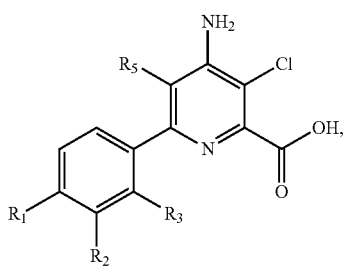

Formula (II)

wherein
R¹ is halogen or methyl;
R² is hydrogen, methyl, or methoxy;
R³ is hydrogen, halogen, or methoxy; and
R⁵ is hydrogen or fluoro,
wherein optionally R¹ and R² can combine to form —OCH₂O—.

3. The method of claim 1, wherein the herbicide is selected from the group consisting of Formula (III) Formula (IV) and their respective salts or esters.

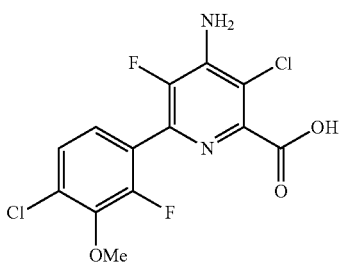

Formula (III)

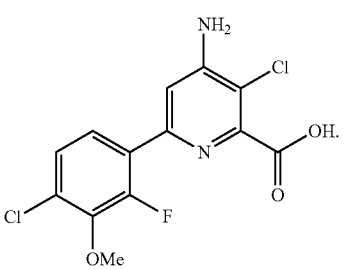

Formula (IV)

4. The method of claim 3, wherein the herbicide is a benzyl ester of Formula (III).

5. The method of claim 3, wherein the herbicide is a methyl ester of Formula (IV).

6. The method of claim 1, wherein the herbicide is selected from the group consisting of Formula (V), Formula (VI), Formula (VII), Formula (VIII), Formula (IX), and their respective salts or esters.

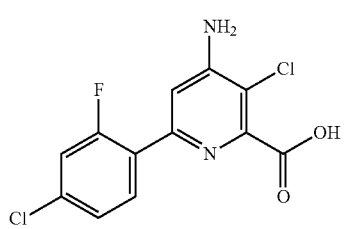

Formula (V)

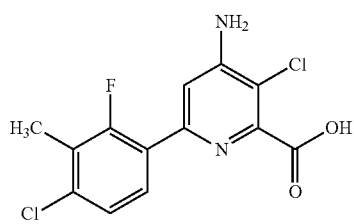

Formula (VI)

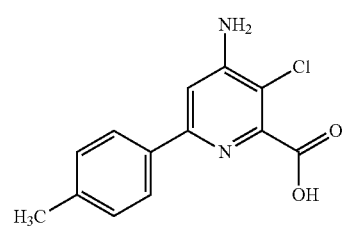

Formula (VII)

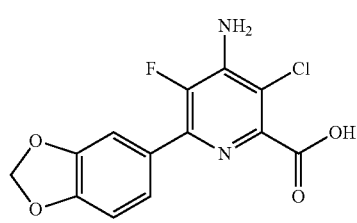

Formula (VIII)

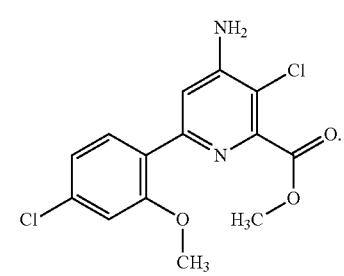

Formula (IX)

7. The method of claim 1, wherein the soybean is infected with soybean rust.

8. The method of claim 1, wherein the broadleaf volunteer crop is a glyphosate tolerant crop.

9. The method of claim 1, wherein the broadleaf volunteer crop contains an AAD-12 gene.

10. The method of claim 1, wherein the broadleaf volunteer crop is ALS resistant.

11. The method of claim 1, wherein the broadleaf volunteer crop is 2,4-D resistant.

12. The method of claim 1, wherein the broadleaf volunteer crop is glufosinate resistant.

13. The method of claim 1, wherein the broadleaf volunteer crop is 4-hydroxyphenyl-pyruvate dioxygenase (HPPD) inhibitor resistant.

14. The method of claim 1, wherein the broadleaf volunteer crop is present in a grassy crop, and the grassy crop is tolerant to the herbicide of Formula (I).

15. The method of claim 14, wherein the herbicide is applied to the broadleaf volunteer crop prior to the emergence of the grassy crop.

16. The method of claim 1, wherein the broadleaf volunteer crop is present in a corn crop, a wheat crop, rice, or fallow.

* * * * *